(12) United States Patent
Harvey

(10) Patent No.: US 11,116,418 B2
(45) Date of Patent: Sep. 14, 2021

(54) MAGNETIC RESONANCE IMAGING AND RADIOTHERAPY APPARATUS WITH AT LEAST TWO-TRANSMIT-AND RECEIVE CHANNELS

(75) Inventor: Paul Royston Harvey, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 806 days.

(21) Appl. No.: 13/884,005

(22) PCT Filed: Nov. 2, 2011

(86) PCT No.: PCT/IB2011/054858
§ 371 (c)(1),
(2), (4) Date: May 8, 2013

(87) PCT Pub. No.: WO2012/063162
PCT Pub. Date: May 18, 2012

(65) Prior Publication Data
US 2013/0225975 A1    Aug. 29, 2013

(30) Foreign Application Priority Data

Nov. 9, 2010  (EP) .................................... 10190476

(51) Int. Cl.
*A61B 5/055*  (2006.01)
*A61N 5/10*  (2006.01)
(Continued)

(52) U.S. Cl.
CPC ............ *A61B 5/055* (2013.01); *A61B 5/0037* (2013.01); *A61N 5/1049* (2013.01);
(Continued)

(58) Field of Classification Search
None
See application file for complete search history.

(56) References Cited

U.S. PATENT DOCUMENTS 6,198,957 B1   3/2001   Green
7,619,413 B2 * 11/2009   Wiggins ................. A61B 5/055
                                                         324/309
(Continued)

FOREIGN PATENT DOCUMENTS

EP    1121957 A2   8/2001
GB    2393373 A    3/2004
(Continued)

OTHER PUBLICATIONS

Hanvey, S. et al "Magnetic Resonance Imaging for Radiotherapy Planning of Brain Cancer Patients using Immobilization and Surface Coils", Physics in Medicine and Biology, Sep. 2009, vol. 52, No. 18, pp. 5381-5394.

(Continued)

*Primary Examiner* — Oommen Jacob
*Assistant Examiner* — Shahdeep Mohammed
(74) *Attorney, Agent, or Firm* — Sherry Austin

(57) ABSTRACT

A therapeutic apparatus comprising a radiotherapy apparatus for treating a target zone and a magnetic resonance imaging system for acquiring magnetic resonance imaging data. The radiotherapy apparatus comprises a radiotherapy source for directing electromagnetic radiation into the target zone. The radiotherapy apparatus is adapted for rotating the radiotherapy source at least partially around the magnetic resonance magnet. The magnetic resonance imaging system further comprises a radio-frequency transceiver adapted for simultaneously acquiring the magnetic resonance data from at least two transmit-and-receive channels. The therapeutic apparatus further comprises a processor and a memory containing machine executable instructions for the processor. Execution of the instructions causes the processor to: calibrate the transmit-and-receive channels; acquire the magnetic resonance data; reconstruct a magnetic resonance (Continued)

image; register a location of the target zone in the image; and generate radiotherapy control signals using the registered image.

20 Claims, 6 Drawing Sheets

(51) Int. Cl.
A61B 5/00 (2006.01)
G01R 33/48 (2006.01)
G01R 33/38 (2006.01)

(52) U.S. Cl.
CPC ........ *G01R 33/4808* (2013.01); *A61N 5/1065* (2013.01); *A61N 5/1069* (2013.01); *A61N 2005/1055* (2013.01); *A61N 2005/1056* (2013.01); *G01R 33/3806* (2013.01); *G01R 33/4812* (2013.01)

(56) References Cited

U.S. PATENT DOCUMENTS

| | | | |
|---|---|---|---|
| 8,958,864 B2 | 2/2015 | Amies et al. | |
| 2001/0049475 A1* | 12/2001 | Bucholz et al. | 600/411 |
| 2007/0108976 A1* | 5/2007 | Morich | G01R 33/4835 324/309 |
| 2007/0241753 A1* | 10/2007 | Sodickson et al. | 324/307 |
| 2008/0007250 A1* | 1/2008 | Wiggins | A61B 5/055 324/200 |
| 2008/0208036 A1 | 8/2008 | Amies | |
| 2009/0124887 A1 | 5/2009 | Roell | |
| 2009/0149735 A1 | 6/2009 | Fallone | |
| 2009/0185981 A1* | 7/2009 | Karczmar et al. | 424/9.3 |
| 2009/0299170 A1 | 12/2009 | Gebhardt et al. | |
| 2010/0137704 A1* | 6/2010 | Vij | A61B 5/0555 600/422 |
| 2010/0167668 A1 | 7/2010 | Nistler | |
| 2010/0292564 A1* | 11/2010 | Cantillon Murphy | G01R 33/4804 600/411 |
| 2010/0305424 A1* | 12/2010 | Cook | A61B 5/055 600/410 |
| 2011/0030698 A1* | 2/2011 | Kaufman | A61B 5/0555 128/845 |
| 2011/0074420 A1* | 3/2011 | Ladebeck | G01R 33/481 324/318 |
| 2011/0087090 A1 | 4/2011 | Boernert et al. | |
| 2011/0218420 A1* | 9/2011 | Carlone | A61N 5/1049 600/411 |
| 2011/0237859 A1* | 9/2011 | Kuhn | A61N 5/1031 600/1 |
| 2011/0247859 A1 | 9/2011 | Kuhn et al. | |
| 2011/0270073 A1* | 11/2011 | Ardenkjaer-Larsen | G01R 33/60 600/410 |
| 2012/0197106 A1* | 8/2012 | Cloos | G01R 33/246 600/411 |

FOREIGN PATENT DOCUMENTS

| | | | |
|---|---|---|---|
| JP | 08112367 A | | 5/1996 |
| WO | 2004024235 A1 | | 3/2004 |
| WO | WO 2008/055531 | * | 5/2008 |
| WO | 2010067287 A1 | | 6/2010 |

OTHER PUBLICATIONS

Raaymakers, B. et al "Note: Integrating a 1.5 T MRI Scanner with a 6MV Accelerator: Proof of Concept; Proof of Concept MRI Accelerator", Physics in Medicine and Biology, vol. 54, No. 12, Jun. 2009, pp. N229-N237.

Bourzac, Katherine, "Radiation Therapy for Moving Targets", Technology Review, Jul. 2009, pp. 1-4.

* cited by examiner

MAGNETIC RESONANCE IMAGING AND RADIOTHERAPY APPARATUS WITH AT LEAST TWO-TRANSMIT-AND RECEIVE CHANNELS

CROSS-REFERENCE TO PRIOR APPLICATIONS

This application is the U.S. National Phase application under 35 U.S.C. § 371 of International Application No. PCT/IB2011/054858, filed on Nov. 2, 2011, which claims the benefit of European Patent Application No. 10190476.1, filed on Nov. 9, 2010. These applications are hereby incorporated by reference herein.

TECHNICAL FIELD

The invention relates to apparatuses for treating a target zone of a subject with radiotherapy, in particular the invention relates to radiotherapy apparatuses guided by magnetic resonance imaging.

BACKGROUND OF THE INVENTION

In routine practice of Radiotherapy (RT), the subject is positioned relative to the stationary center of the rotating arc carrying the RT source. Positioning implies both height and lateral adjustment of the subject table. This positioning is required to optimize the dose in the lesion beyond variation that can be obtained by applying RT rays from different angles.

Integration of MR and Linear Accelerators (LINAC) opens new horizons in Radiotherapy by improved lesion targeting, especially for moving organs. In a practical implementation proposal, the LINAC rotates around the subject to hit the gross target volume (GTV) and clinical target volume (CTV) from multiple angles while minimizing the radiation exposure for surrounding tissues.

The combination of magnetic resonance apparatuses and LINAC radiotherapy sources is known. Typically a LINAC source is placed on a rotating gantry about the magnet and designing the magnet such that the LINAC rotates in a zero-field region of the magnet. Another particular feature of the concept is the use of a split gradient coil which prevents attenuation of the LINAC beam.

U.S. Pat. No. 6,198,957 discloses a radiotherapy machine for beam treating a region of a subject combined with a magnetic resonance imaging system. The beam and the excitation coil assembly of the imaging system are arranged so that the beam is not incident on the coil assembly.

While performing radiotherapy the radiotherapy source is typically moved to a variety of positions while irradiating a target zone. This is done to minimize the exposure portions of a subject which do not include the target zone to the effects of the radiation. Typically, this is done by rotating the radiotherapy source about an axis of rotation.

SUMMARY OF THE INVENTION

The invention provides for a therapeutic apparatus, a computer program product, and a method of controlling a therapeutic apparatus in the independent claims. Embodiments are given in the dependent claims.

A difficulty encountered in guiding radiotherapy treatments using magnetic resonance (MR) imaging is the limited space in magnets that are useful for clinical imaging, such as cylindrical superconducting magnets. For such magnets there is simply is not sufficient space in a magnet to position the target zone along the rotational axis of the radiotherapy source.

Some embodiments of the invention address this problem by eliminating the use of a volume body coil from the magnetic resonance imaging system. The volume body coil is replaced by a least two transmit-and-receive-coils. This may have the advantage that the space normally used by a volume body coil is available for moving the subject within the magnet. This may allow more positioning of the subject such that a target zone is located at a rotational axis of a radiotherapy source.

The invention disclosure describes a novel MRI guided Radiotherapy system that is compatible with state-of-the-art subject handling systems that are currently used with Linear Accelerator (LINAC) therapy systems. The following aspects of the system may enable free positioning of the subject with respect to the LINAC focal point and the acquisition of MRI data without the use of an in-built body coil in a manner that is compatible with the use of a state-of-the-art carbon fiber table top while avoiding physical interference of RF coils with the therapy beam. Embodiments of the inventions described herein may represent improvements upon the existing MR-LINAC system concept which utilizes a LINAC apparatus rotating about a common iso-center within a zero-field region of an MRI magnet. The key features may be:

1) No built in body coil frees up space within the system bore that enable free 6 dimensional movement of the subject required for positioning target anatomies at the center of rotation of the LINAC beam as required for optimum therapeutic efficacy.
2) The magnet and gradient coil are designed to realize a ≥80 cm free bore in which the subject can be freely positioned. For an 80 cm bore inside the gradient coil it is expected that a 96 cm inner diameter magnet will suffice.
3) In place of the built in RF body coil, local transmit/receive RF coils or a split multi-element Tx/Rx array are used such that the subject can be surrounded by the elements while maintaining a suitable gap which avoids beam interference. Since the local coil arrays are placed on the table top, as opposed to surrounding it, the method is fully compatible with a carbon fiber table top. Since the coils are directly on the subject they are free to move with the subject and more efficient with respect to RF power demand.
4) The multi-element Tx/Rx array coils are used in transmit mode for MR excitation. By the use of RF shimming it is possible to focus the excitation at the target anatomy and also to focus the reception sensitivity of the coil to the same target anatomy thereby maximizing SNR.
5) Due to the extra large MR system bore it is possible to utilize existing LINAC subject positioning methods which enable 6 dimensional placement of the subject with target anatomy at system iso-center, as desired for optimum therapeutic efficacy.
6) To maximize the efficiency of the LINAC beam it is also proposed to optionally introduce an external recess in the magnet in order that the LINAC beam can be placed closer to the subject.

A 'computer-readable storage medium' as used herein encompasses any tangible storage medium which may store instructions which are executable by a processor of a computing device. The computer-readable storage medium may be referred to as a 'computer-readable non-transitory storage medium.' The computer-readable storage medium may also be referred to as a 'tangible computer readable medium.' In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM) memory, Read Only Memory (ROM) memory, an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'computing device' or 'computer system' as used herein refers to any device comprising a processor. A 'processor' is an electronic component which is able to execute a program or machine executable instruction. References to the computing device comprising "a processor" should be interpreted as possibly containing more than one processor. The term computing device should also be interpreted to possibly refer to a collection or network of computing devices each comprising a processor. Many programs have their instructions performed by multiple processors that may be within the same computing device or which may even distributed across multiple computing device.

A 'user interface' as used herein encompasses an interface which allows a user or operator to interact with a computer or computer system. A user interface may provide information or data to the operator and/or receive information or data from the operator. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of receiving information or data from an operator.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance data. This visualization can be performed using a computer.

A 'volume body coil' or 'body coil' as used herein encompasses a radiofrequency antenna used to excite or manipulate the orientation of magnetic spins as preparation for the acquisition of magnetic resonance data.

A 'transmit-and-receive channel' as used herein encompasses an antenna which is used to both excite or manipulate the orientation of magnetic spins as preparation for the acquisition of magnetic resonance data and for the acquisition of magnetic resonance data.

In one aspect the invention provides for a therapeutic apparatus comprising a radiotherapy apparatus for treating a target zone of a subject. The radiotherapy apparatus comprises a radiotherapy source for directing electromagnetic radiation into the target zone. The electromagnetic radiation may be high energy photons generated for example but not limited to: an x-ray source, a LINAC x-ray source, and a radioisotope gamma radiation source. A radioisotope gamma radiation source as used herein encompasses a radiation source for generating gamma radiation that uses a radioisotope.

The therapeutic apparatus further comprises a magnetic resonance imaging system for acquiring magnetic resonance imaging data from an imaging zone. The target zone is within the imaging zone. The magnetic resonance imaging system comprises a magnet for generating a magnetic field within the imaging zone. The radiotherapy apparatus is adapted for rotating the radiotherapy source at least partially around the magnet. The magnetic resonance imaging system further comprises a radio-frequency transceiver adapted for simultaneously acquiring the magnetic resonance data from at least two transmit-and-receive channels. As used herein a channel refers to an antenna. The channels may comprise multiple coils or antenna elements.

The therapeutic apparatus further comprises a processor for controlling the therapeutic apparatus. A processor as used herein encompasses a computer system with one or more processors and it may also encompass computer systems with multiple processors. The therapeutic apparatus further comprises a memory containing machine executable instructions for execution by the processor.

Execution of the instructions causes the processor to perform a pre-scan calibration of the at least two transmit-and-receive channels using the magnetic resonance imaging system. During the pre-scan calibration magnetic resonance data is acquired for each of the at least two transmit-and-receive channels. The individual transmit-and-receive channels could for example be placed on the subject in different positions. They may be placed such that the radiotherapy apparatus does not direct the electromagnetic radiation into the transmit-and-receive channels. By performing a pre-scan calibration of the at least two transmit-and-receive channels their placement is not critical. The pre-scan calibration may be used for determining the phases and amplitudes for transmitting and receiving radio signals from magnetic spins in the imaging zone.

Execution of the instructions further causes the processor to acquire the magnetic resonance data in accordance with the pre-scan calibration using the at least two transmit-and-receive channels. This may include the phase and amplitudes of individual coil elements of each of the transmit-and-receive channels and also the phase and amplitude corrections for received radio signals by each coil or element of the at least two transmit-and-receive channels. Execution of the instructions further causes the processor to reconstruct a magnetic resonance image from the magnetic resonance data. It is understood herein that a magnetic resonance image may refer to multiple magnetic resonance images. For instance the magnetic resonance data may be acquired primarily from a particular volume. A series of magnetic resonance images may be constructed to represent the volume from which the magnetic resonance data is primarily acquired. The magnetic resonance image is typically reconstructed using Fourier techniques. For this reason volumes outside of the image may also contribute to the magnetic resonance image due to the Fourier techniques.

Execution of the instructions further causes the processor to generate radiotherapy control signals in accordance with the location of the target zone. The radiotherapy control signals cause the radiotherapy source to irradiate the target zone. The radiotherapy control signals may also cause the radiotherapy source to be positioned by the radiotherapy apparatus. The radiotherapy apparatus may for instance contain a ring or other positioning mechanisms or elements for physically moving the radiotherapy source. In this case the radiotherapy control signals control both whether the radiotherapy source is generating radiation and the position of the radiotherapy source.

Execution of the instructions further cause the processor to send the radiotherapy control signals to the radiotherapy system. Sending the radiotherapy control signals may be performed in different ways depending upon the embodiment. For instance the processor may send control signals to a separate controller or a computer which controls the radiotherapy apparatus. In other embodiments a hardware interface is used such that the processor controls and sends control signals to the radiotherapy system directly.

In another embodiment the radiotherapy apparatus contains a rotation mechanism for rotating the radiotherapy source around a rotational axis. In another embodiment the radiotherapy source directs the radiation through the rotational axis. In another embodiment the magnetic resonance imaging system has an axis. In another embodiment the rotational axis of the radiotherapy apparatus and the axis of the magnet of the magnetic resonance imaging system are coaxial.

In another embodiment the therapeutic apparatus further comprises a subject support. The subject support comprises a mechanical positioning system for positioning the subject within the magnet. In different embodiments the subject support is capable of moving with a varying number of degrees of freedom. In some embodiments a mechanical positioning system has six degrees of freedom. The support may move in three spatial directions and also be able to rotate about an axis for each of those directions. This embodiment allows the free placement of a subject such that the target zone is treated optimally.

In another embodiment the radiotherapy source rotates about an axis of rotation. Execution of the instructions further causes the processor to generate positioning control signals that cause the mechanical positioning system to move the target zone to the axis of rotation. The positioning control signals are generated in accordance with the location of the target zone in the registered magnetic resonance image. Execution of the instructions further cause the processor to send the positioning control signals to the mechanical positioning system. This embodiment is advantageous because if the radiotherapy source rotates about an axis of rotation and the target zone is placed in the axis of rotation then the radiotherapy source will always be in a position to irradiate the target zone. This may minimize the amount of electromagnetic radiation which is directed into regions of the subject which are not part of the target zone.

In another embodiment the radiotherapy source directs electromagnetic radiation through the rotational axis.

In another embodiment the therapeutic apparatus comprises the at least two transmit-and-receive channels. The at least two transmit-and-receive channels are part of the therapeutic apparatus in this embodiment.

In another embodiment each of the transmit-and-receive channels has multiple coil elements. Execution of the instructions further causes the processor to calibrate the send amplitudes and phases and the receive amplitudes and phases for the multiple coil elements during the pre-scan calibration. This may be performed by acquiring magnetic resonance data which each coil element for each of the transmit-and-receive channels and then performing a fitting procedure to determine the best amplitudes and phases to use for both sending signals and receiving signals using the transmit-and-receive channels.

In another embodiment the at least two transmit-and-receive channels comprise flexible coil elements. This embodiment is particularly advantageous because the transmit-and-receive channels can then be placed directly on the subject. As they may then conform to the outer shape of the subject, the at least two transmit-and-receive channels will occupy less space. This allows more room in the magnet and allows for more freedom in controlling the positioning of the subject, for instance if the therapeutic apparatus comprises a subject support then the subject support will have more space in which to move the subject.

In another embodiment execution of the instructions further causes the processor to repeatedly acquire the magnetic resonance data, repeatedly reconstruct the magnetic resonance image, and repeatedly register the location of the target zone during irradiation of the target zone. Execution of the instructions further cause the processor to repeatedly generate and send repeatedly updated radiotherapy control signals. The updated radiotherapy control signals compensate for motion of the subject between subsequent acquisitions of the magnetic resonance data. Execution of the instructions further causes the processor to repeatedly send the updated radiotherapy control signals to the radiotherapy source during irradiation of the target zone. In some embodiments the positioning control signals may also be repeatedly generated and repeatedly sent to the mechanical positioning system.

Repeatedly acquiring the magnetic resonance data and then compensating for motion of the subject either internal or external may be beneficial because the target zone is irradiated more accurately and there is a reduced chance that portions of the subject which are not part of the target zone are irradiated by mistake.

In another embodiment the radiotherapy source comprises an adjustable beam collimator. The adjustable beam collimator may for instance be a multi leaf collimator. The updated radiotherapy control signals comprise commands for controlling the beam collimator. For instance the beam collimator may move a series of plates or other material which attenuates the magnetic radiation generated by the radiotherapy source. By adjusting the plates the magnetic radiation beam directed at the target signal may be controlled. This is advantageous because the path of the beam may be controlled without moving the radiotherapy source rotationally or in some embodiments moving the mechanical positioning system.

In another embodiment a radio-frequency excitation field manipulating the orientation of the magnetic spins in an imaging zone is generated exclusively by the at least two transmit-and-receive channels. This embodiment may be particularly advantageous because a radio-frequency volume body coil is not used for creating the radio-frequency excitation field. This provides more space within the imaging zone of the magnet for moving the subject.

In another embodiment the magnetic resonance imaging system does not comprise a radio-frequency volume body coil.

In another embodiment the magnet is a cylindrical superconducting magnet. The magnet has a recess in an outer wall. The radiotherapy apparatus is adapted for rotating the radiotherapy source around or about the recess. At least a portion of the radiotherapy source is within the recess. This embodiment is advantageous because the radiotherapy source is positioned closer to the subject. This may have the benefit of positioning the radiotherapy source within a low magnet field zone of the magnet. It may also have the advantage that a less accurate adjustable beam collimator is needed for accurately controlling the electromagnetic radiation directed into the target zone. This may reduce the cost of the therapeutic apparatus.

In another embodiment the radiotherapy apparatus comprises a light source for illuminating a portion of the subject that is descriptive of the path of radiation generated by the radiotherapy source. This embodiment is advantageous because an operator or healthcare provider positioning a subject in the therapeutic apparatus can see if anything will block the path of the electromagnetic radiation generated by the radiotherapy source. For instance the at least two transmit-and-receive channels can be positioned on the subject and then checked with the light source to see if the radiation beam will hit the receive channels. If the light does contact the receive channels then the at least two transmit-and-receive channels can be repositioned.

In another embodiment the radiotherapy source is a LINAC x-ray source. In another embodiment the radiotherapy source is an x-ray tube. In another embodiment the radiotherapy source is a radioisotope gamma radiation source.

In another embodiment the radiotherapy source is a LINAC for generating x-ray or gamma radiation. The magnet is adapted for generating a low magnetic field zone which encircles the magnet. The radiotherapy apparatus is adapted such that the radiotherapy source rotates about the magnet within the low magnetic field zone. The magnetic field strength within the low magnetic field zone is below an operational threshold of the LINAC source. The operational threshold defines a magnetic field strength which prevents the LINAC source from functioning properly. In modern cylindrical bore magnetic resonance imaging magnets there are typically several compensation coils. The compensation coils generate a magnetic field which is opposed to coils used to generate the main magnetic field. This results in an area outside of the cylindrical magnet approximately in the mid-plane which is doughnut-shaped and has a low magnetic field. The low magnetic field zone may be this doughnut-shaped zone surrounding the cylindrical magnet with compensation coils.

In another embodiment the operational threshold is below 50 gauss, preferably below 10 gauss.

In another aspect the invention provides for a computer program product comprising machine executable instructions for execution by a processor of a radiotherapy apparatus. For instance the computer program product may be stored on a computer-readable storage medium. The therapeutic apparatus comprises a radiotherapy apparatus for treating a target zone of a subject. The radiotherapy apparatus comprises a radiotherapy source for directing electromagnetic radiation into the target zone.

The therapeutic apparatus further comprises a magnetic resonance imaging system for acquiring magnetic resonance imaging data from an imaging zone. The target zone is within the imaging zone. The magnetic resonance imaging zone comprises a magnet for generating a magnetic field within the imaging zone. The radiotherapy apparatus is adapted for rotating the radiotherapy source at least partially around the magnet. The magnetic resonance imaging system further comprises a radio-frequency transceiver adapted for simultaneously acquiring the magnetic resonance data from at least two transmit-and-receive channels. Execution of the instructions causes the processor to perform a pre-scan calibration of the at least two transmit-and-receive channels using the magnetic resonance imaging system.

Execution of the instructions further causes the processor to acquire the magnetic resonance data in accordance with the pre-scan calibration using the at least two transmit-and-receive channels. Execution of the instructions further causes the processor to reconstruct a magnetic resonance image from the magnetic resonance data. Execution of the instructions further causes the processor to register a location of the target zone in the magnetic resonance image. Execution of the instructions further causes the processor to generate radiotherapy control signals in accordance with the location of the target zone. The radiotherapy control signals cause the radiotherapy source to irradiate the target zone. Execution of the instructions further causes the processor to send the radiotherapy control signals to the radiotherapy system.

The invention also provides for a computer-readable storage medium containing a computer program product according to an embodiment of the invention.

The invention also provides for a method of controlling a therapeutic apparatus. The method and embodiments of the method herein may also be implemented as a computer-implemented method. The therapeutic apparatus comprises a radiotherapy apparatus for treating a target zone of a subject. The radiotherapy apparatus comprises a radiotherapy source for directing electromagnetic radiation into the target zone.

The therapeutic apparatus further comprises a magnetic resonance imaging system for acquiring magnetic resonance imaging data from an imaging zone. The target zone is within the imaging zone. The magnetic resonance imaging system comprises a magnet for generating a magnetic field within the imaging zone. The radiotherapy apparatus is adapted for rotating the radiotherapy source at least partially around the magnet. The magnetic resonance imaging system further comprises a radio-frequency transceiver adapted for simultaneously acquiring the magnetic resonance data from at least two transmit-and-receive channels.

The method comprises the step of performing a pre-scan calibration of the at least two transmit-and-receive channels using the magnetic resonance imaging system. The method further comprises the step of acquiring the magnetic resonance data in accordance with the pre-scan calibration using the at least two transmit-and-receive channels. The method further comprises the step of reconstructing a magnetic resonance image from the magnetic resonance data. The method further comprises the step of registering a location of the target zone in the magnetic resonance image. The method further comprises the step of generating radiotherapy control signals in accordance with the location of the target zone. The radiotherapy control signals cause the radiotherapy source to irradiate the target zone. The method further comprises the step of sending the radiotherapy control signals to the radiotherapy system.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
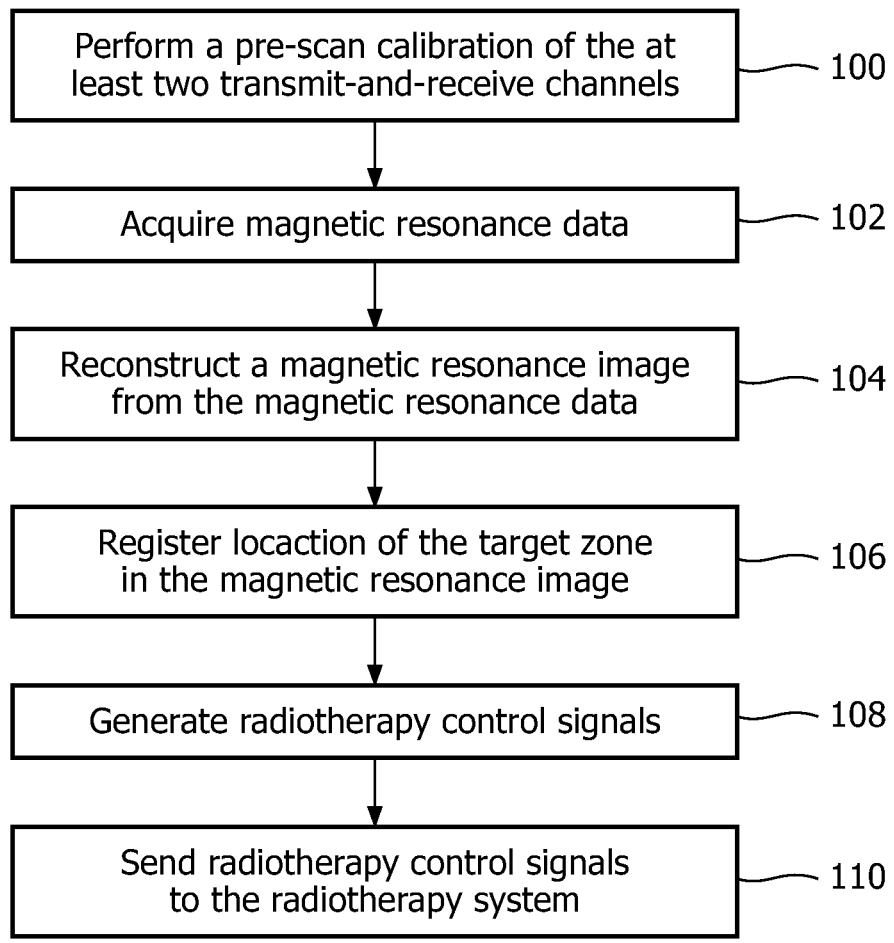
FIG. 1 shows a flow diagram which illustrates a method according to an embodiment of the invention.

FIG. 1 shows a full flow diagram which illustrates an embodiment of a method according to the invention. In step 100 a pre-scan calibration of the at least two transmit-and-receive channels is performed. In step 102 magnetic resonance data is acquired. The magnetic resonance data is acquired using a calibration that was determined in step 100. Next in step 104 a magnetic resonance image is reconstructed from the magnetic resonance data. The magnetic resonance image may be one or a collection of magnetic resonance images. In step 106 the location of the target zone is registered in the magnetic resonance image. In step 108 radiotherapy control signals are generated. In step 110 the radiotherapy control signals are sent to the radiotherapy system. Sending the radiotherapy control signals to the radiotherapy system causes the radiotherapy system to perform a therapeutic operation on the subject.

Figure 2:
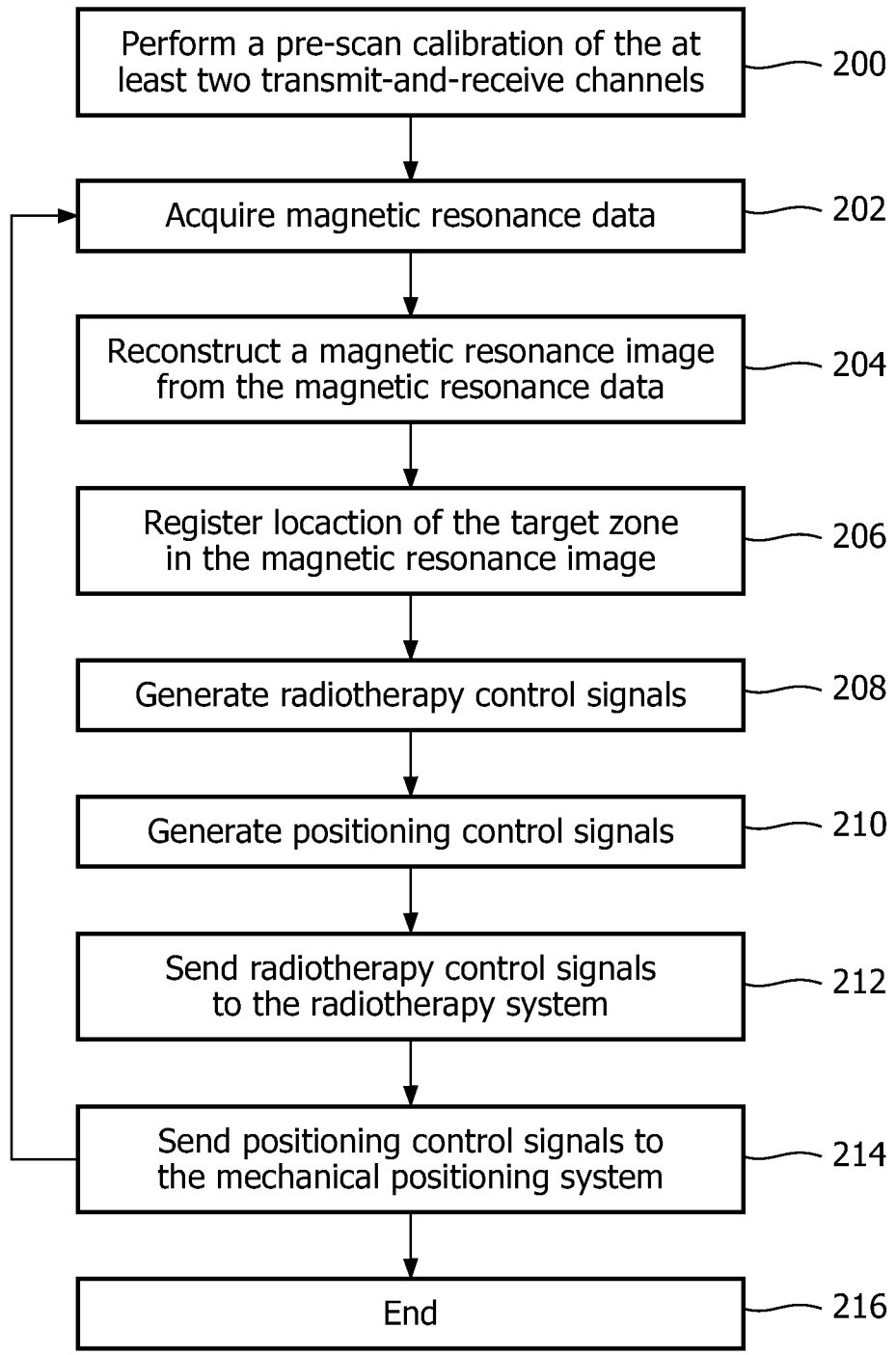
FIG. 2 shows a flow diagram which illustrates a method according to a further embodiment of the invention.

FIG. 2 shows a flow diagram which illustrates a method according to a further embodiment of the invention. In step 100 a pre-scan calibration is performed for the at least two transmit-and-receive channels. In step 2 magnetic resonance data is acquired. In step 204 a magnetic resonance image is reconstructed from the magnetic resonance data. In step 206 a location of the target zone in the magnetic resonance image is registered. Step 206 is equivalent to step 106 in FIG. 1. The registration may be performed by any number of known registration techniques. For instance a deformable model may be fit to one or more magnetic resonance images. Also specialized algorithms which detect anatomical features in the magnetic resonance may be used also. The located anatomical features or the deformable model may be used to fine the location of the target zone. In step 208 radiotherapy control signals are generated. In step 210 positioning control signals are generated.

The radiotherapy control signals and the positioning control signals are generated in conjunction with each other. As both sets of control signals are needed to position the target zone such that the radiotherapy source is able to irradiate it. Next in step 212 the radiotherapy control signals are sent to the radiotherapy system. In step 214 positioning control signals are sent to the mechanical positioning system. In this flow diagram there is an arrow that looks back from step 214 to step 202. This indicates that during process of the target zone magnetic resonance data may be repeatedly acquired and used to repeatedly generate radiotherapy control signals and positioning control signals. This may be repeated repeatedly until the therapy ends in step 216.

Figure 3:
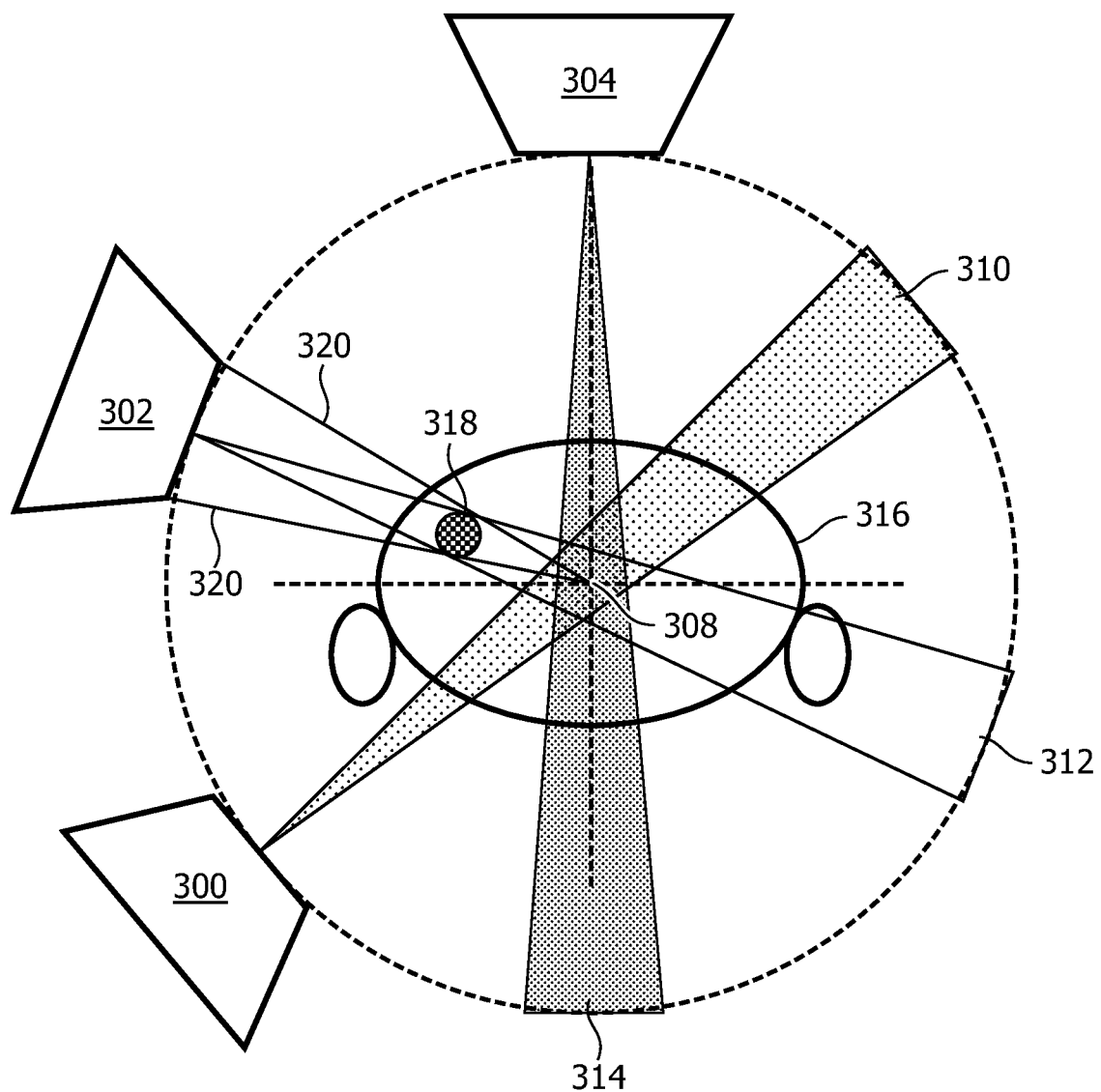
FIG. 3 shows a diagraph which illustrates the positioning of a radiotherapy source relative to a target zone of a subject.

FIG. 3 shows a cross-sectional view of some components of a therapeutic apparatus. Shown are a radiotherapy source in a first position 300, a second position 302, and a third position 304. The dashed line labeled 306 shows the path of rotation of the radiotherapy source 300, 302, 304. The point labeled 308 indicates the axis of rotation 308. The region labeled 310 is the radiation beam generated by the radiotherapy source in the first position 300. The region labeled 312 shows the path of the radiation beam generated by the radiotherapy source in the second position 302. The region labeled 314 shows a path of the radiation beam when the radiotherapy source in the third position 304. Sitting in the center of the diagram is a subject 316 with a target zone 318 that is off axis with regard to the axis of rotation 308. The lines 320 indicate the angular range of the radiotherapy source 302 where the radiotherapy source 302 will be able to irradiate the target zone 318 with radiation.

In this Fig. it is quite clear that the treatment options are very limited. In addition regions of the subject 316 which are not for the target zone 318 will be irradiated also. If for instance the radiation beam is used to kill a cancer located in the target zone 318 it is very likely that a large amount of healthy tissue surrounding the target zone 318 would also be killed or damaged. If the subject 316 is within a magnetic resonance imaging system without much clearance then it is clear that it will not be feasible to have the target zone 318 located at the axis of rotation 308.

Figure 4:
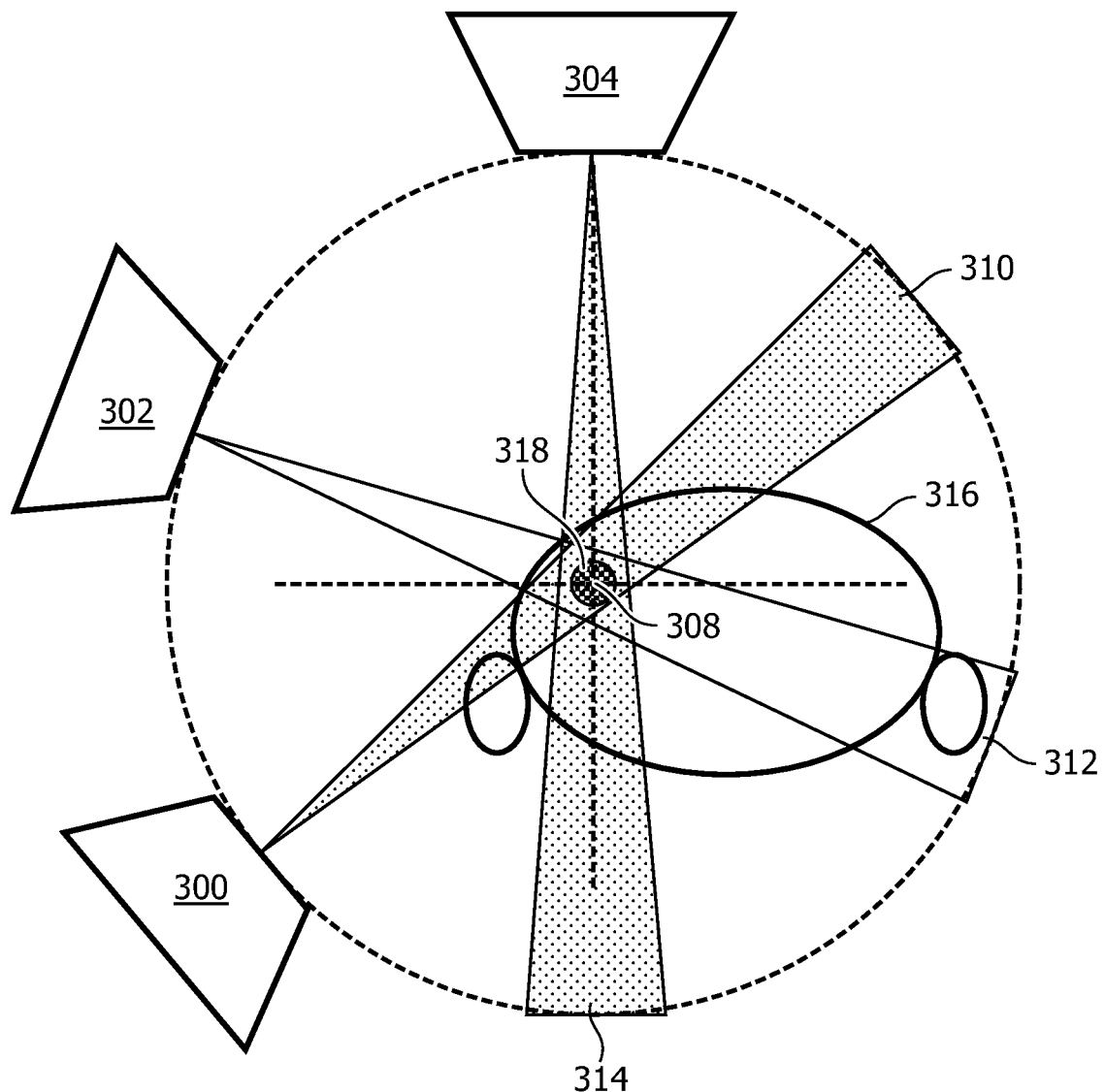
FIG. 4 shows a diagraph which further illustrates the positioning of a radiotherapy source relative to a target zone of a subject.

FIG. 4 shows a diagram which is identical to FIG. 3 except the subject 316 has been moved such that the target zone 318 is now located at the axis of rotation 308. In examining this Fig. it is clear that the target zone 308 will be treated regardless of what position the radiotherapy source 300, 302, 304 is in. FIG. 4 illustrates the benefit of being able to move a subject within a magnetic resonance imaging system for positioning the target zone 318 on the axis of rotation 308.

Figure 5:
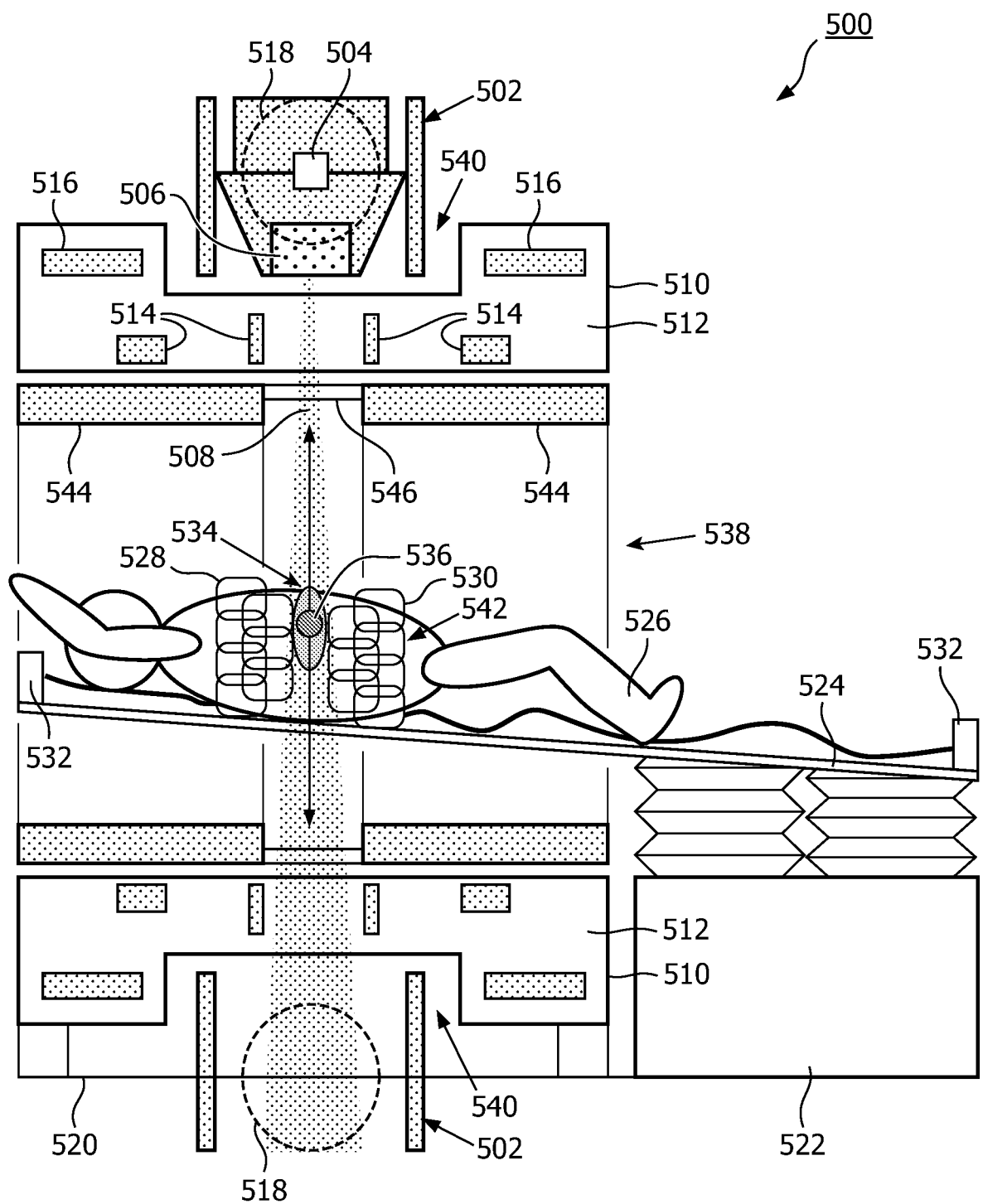
FIG. 5 shows a diagraph which further illustrates the positioning of a radiotherapy source relative to a target zone of a subject.

FIG. 5 shows an embodiment of a therapeutic apparatus 500 according to an embodiment of the invention. In FIG. 5 there is a radiotherapy apparatus 502. Within the radiotherapy apparatus 502 is a radiotherapy source 504. Below the radiotherapy source 504 is an adjustable beam collimator 506. The radiotherapy source 504 generates a radiation beam 508. The therapeutic apparatus 500 also comprises a magnetic resonance imaging system. The radiotherapy apparatus 502 forms a ring around a magnet 510 of the magnetic resonance imaging system. The magnet is a superconducting magnet with a cryostat 512. There are superconducting coils 514 for generating a magnetic field for the magnet. There are superconducting shield coils 516 which generate a low magnetic field region 518. The radiotherapy source 504 is shown as being located within the low field region 518. The low field region 518 forms a doughnut surrounding the cylindrical magnet 510.

The magnet 510 is shown as resting on the floor 520. Adjacent to the magnet 520 is a six-dimensional positioning system 522 for a subject support 524. A subject 526 is shown as reposing on the subject support 524. On either side of the radiation beam 508 is shown a first transmit-and-receive channel 528 and a second transmit-and-receive channel 530. Both the first 528, and second transmit-and-receive channels are connected to a transceiver 532. The transceiver in this embodiment is shown as two separate transceivers 532 but may also be a single unit which both channels 528, 530 are connected to. Between the first 528 and second 530 transmit-and-receive channels is imaging zone 534. The target zone 536 of the subject 526 is shown as being located within the imaging zone 534. The space within the magnet 510 for receiving the subject 526 is the bore 538 of the magnet. The rotational axis 542 is also the axis of symmetry for the magnet 510 in this example.

In this example the magnet has a large bore. For some embodiments, a six-dimensional positioning system 522 is beneficial if the magnet has a bore of 80 cm or greater. This allows the target zone 536 to be positioned efficiently such that the target zone 536 is accessible by the radiation beam 508 and is positioned on the rotational axis 542. The dashed line pointed to by arrow 542 is the rotational axis. In this embodiment the magnet 510 has a recess 540 which allows the radiotherapy source 504 to be positioned closer to the subject 526. Also shown within the bore 538 of the magnet 510 is a magnetic field gradient coil 544. The magnet field gradient coil 544 is shown as being a split type with a gap 546 in the magnet field gradient coil. The gap 546 may be a region with a reduced number or no conductors from the coil. In this example the gradient coil 544 is shown as one assembly. However, typically magnet field gradient coils contain three separate gradient systems for spatially encoding spins within the imaging zone 534.

Embodiments constructed in accordance with FIG. 5 may have several features. The first feature (1) is to eliminate the volume RF body coil. This frees up space which can be used to enable a larger degree of subject positioning.

The next feature (2) specifies an inner system bore size of at least 80 cm. By eliminating the RF body coil this saves approximately 6 cm of subject bore and consequently this results in a smaller magnet and gradient coil bore thereby reducing cost and power requirements.

The third feature (3) is to always use local and multi-element RF transmit (Tx) receive (Rx) coils. Local Tx/Rx coil can be placed around the subject for maximum sensitivity and are always placed on top of the table thereby avoiding the problems associated with using a carbon fiber table top. From the RF perspective, local coils can be made compatible with continued use of a carbon fiber tabletop as preferred for LINAC therapy.

The next feature (4) uses multiple groups of multi-element multi-channel Tx/Rx coils which can be placed around the subject while avoiding the path of the LINAC therapy beam. Due to the multi-channel transmit capability it is now possible to focus the transmit and receive field to the target anatomy thereby obtaining maximum efficiency/sensitivity despite the physical gap allowed for the therapy beam.

By widening the magnet bore and enabling re-use of the carbon fiber table top it is now possible (5) to use subject table technology that can position the subject accurately at MRI and therapy iso-center.

The final feature of this innovation (6) is to recess the outer canister of the magnet thereby enabling closer proximity of the LINAC gantry to the subject for better efficiency of the LINAC beam.

Figure 6:
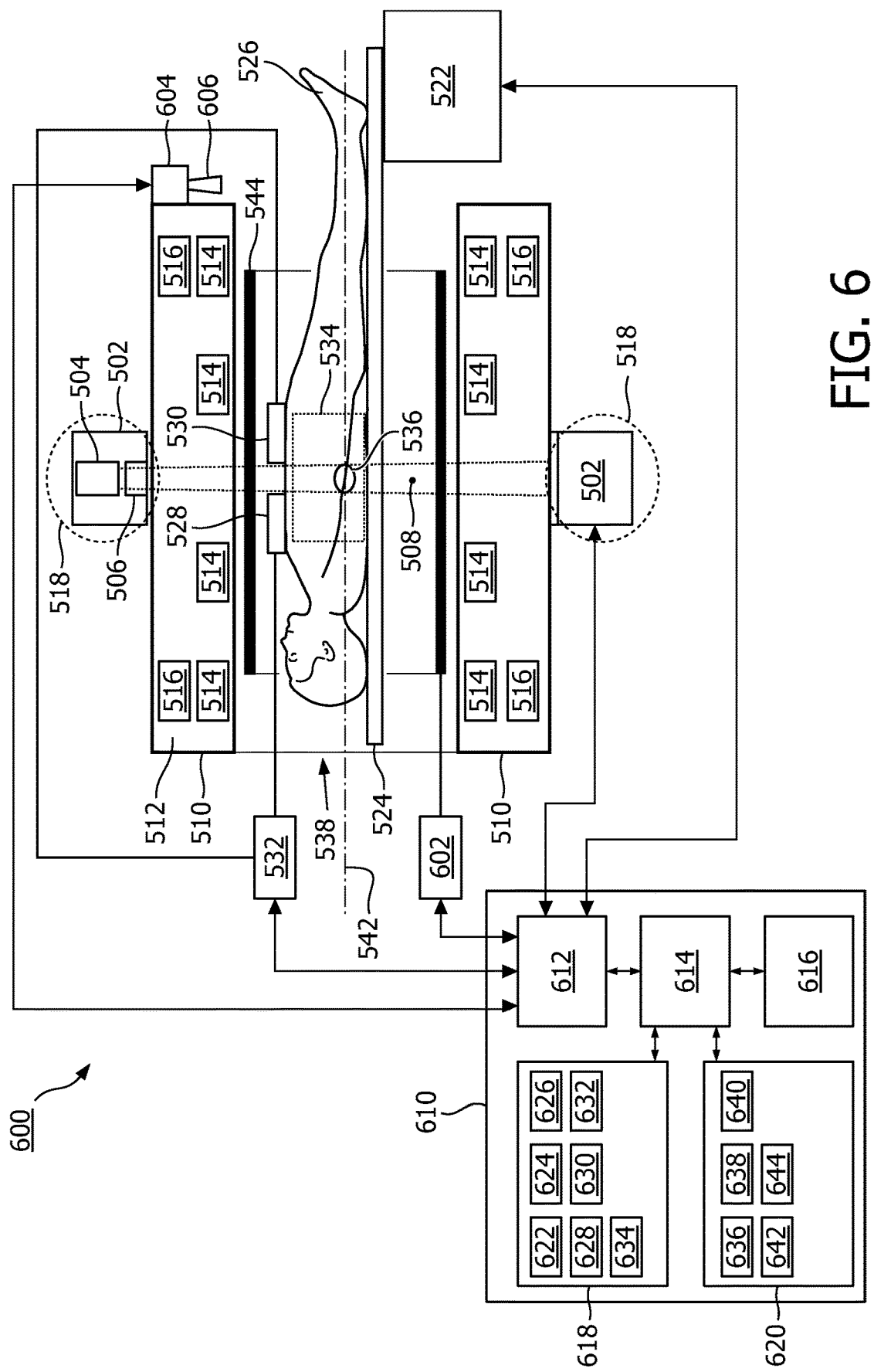
FIG. 6 shows a diagram which illustrates a therapeutic apparatus according to an embodiment of the invention.

FIG. 6 shows a further embodiment of a therapeutic apparatus 600 according to an embodiment of the invention. The therapeutic apparatus shown in FIG. 6 is essentially equivalent to that shown in FIG. 5. In the embodiment shown in FIG. 6 there is no recess shown in the magnet 510 as is shown in FIG. 5. However a recess could easily be incorporated into the embodiment shown in FIG. 6 also. Also in comparison to FIG. 5 there is no gap in the magnetic field gradient coil 544. However, such a magnetic field gradient coil could also be incorporated into the embodiment shown in FIG. 6. The magnetic field gradient coil 544 is shown as being connected to a magnetic field gradient coil power supply which is adapted for supplying current to the magnetic field gradient coil.

In the embodiment shown in FIG. 6 a single transceiver 532 is connected to the first 528 and second 530 transmit-and-receive channels. There is a computer system 610 with a processor 614 for controlling the operation and function of the therapeutic apparatus 600. Connected to the processor 614 is a hardware interface 612 which interfaces to the magnet field gradient power supply 602, the radio-frequency transceiver 532 and the radiotherapy apparatus 502.

The hardware interface 612 is also connected to an optional light source 604. The light source has a light collimator 606 and is mounted onto an edge of the magnet 510. The light source can be controlled by the processor 614 such that when the subject 526 is retracted from the magnet 510 the light source can show where the radiation beam 508 will impinge on the subject 526. This could be used for instance to determine if the radiation will hit either the first 528 or second 530 transmit-and-receive channel. The light source 604 is mounted on the outside of the magnet 510 because an operator or healthcare professional placing the transmit-and-receive channels 528, 530 would not be able to see them within the bore 538 of the magnet 510. The light source 604 could for instance be mounted on a rail which goes along the outside edge of the magnet 510. This could be used to circle the subject 526 and show where the radiation beam 508 will hit the subject 526 when the subject 526 is placed into the bore 538 of the magnet 510.

The processor 614 is further connected to a user interface 616 which allows an operator to control the functionality of the therapeutic apparatus 600. The processor 614 is also connected to computer storage 618 and computer memory 620. The computer storage 618 is shown as containing a treatment plan 622. The treatment plan 622 contains instructions or details for performing therapy on the target zone 536. The treatment plan may contain anatomical instructions and durations or times and energies of radiation 508 to be impinged on the target zone 536. Also shown in the computer storage is magnetic resonance data 624 acquired using the therapeutic apparatus 600. Also shown within the computer storage 618 is a magnetic resonance image 626 which has been reconstructed from the magnetic resonance data 624. Further shown within the computer storage 618 is a registered location of a target zone 628. The registered location 628 is a description in terms of the therapeutic apparatus' internal coordinates of the location of the target zone 536.

The computer storage 618 is further shown as containing radiotherapy control signals 630 and positioning control signals 632. The radiotherapy control signals 630 are for controlling the radiotherapy apparatus 502 and the positioning control signals 632 are for controlling the subject support 524 and the six-dimensional positioning system 522. Further shown within the computer memory 618 is a channel calibration 634. The channel calibration 634 contains phase and/or amplitude calibrations for the sending and/or receiving of radio-frequency signals using the two channels. The transmit-and-receive channels may contain individual antenna or coil elements. The channel calibration 634 contains phase and/or amplitude calibrations for these individual coil or antenna elements. The computer memory 620 is shown as containing a therapeutic control system module 636. The therapeutic control system module 636 is executable code for controlling the operation and function of the therapeutic system. Further, in some embodiments it may convert the treatment plan 622 into radiotherapy control signals 630 and positioning control signals 632.

The computer memory 620 is further shown as containing an image reconstruction module 638. The image reconstruction module 638 contains executable code for transforming the magnetic resonance data 624 into a magnetic resonance image 626. The computer memory 620 is further shown as containing an image registration module 640. The image registration module 640 contains computer executable code for performing a registration on the magnetic resonance image 626 and generating the registered location of the target zone 628. The computer memory 620 is further shown as containing a planning module 642. The planning module may use the image registration module 642 and the treatment plan 622 to generate the radiotherapy control signals 630 and/or the positioning control signals 632. The computer memory 620 is further shown as containing a pre-calibration module 644. The pre-calibration module 644 contains computer executable code for performing and generating the channel calibration 634. Functions not discussed in modules 638, 640, 642, and 644 are performed by the therapeutic control system module 636.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 radiotherapy source in first position
302 radiotherapy source in second position
304 radiotherapy source in third position
306 path of rotation
308 axis of rotation
310 radiation beam in first position
312 radiation beam in second position
314 radiation beam in third position
316 subject
318 target zone
320 angular zone
500 therapeutic apparatus
502 radiotherapy apparatus
504 radiotherapy source
506 adjustable beam collimator
508 radiation beam
510 magnet
512 cryostat
514 superconducting coil
516 shield coil
518 low field region
520 floor
522 six dimensional positioning system
524 subject support
526 subject
528 first transmit-and-receive channel
530 second transmit-and-receive channel
532 transceiver
534 imaging zone
536 target zone
538 bore of magnet
540 recess
542 rotational axis
544 magnetic field gradient coil
546 gap in magnetic field gradient coil
600 therapeutic apparatus
602 magnetic field gradient coil power supply
604 light source
606 light collimator
610 computer system
612 hardware interface
614 processor
616 user interface
618 computer storage
620 computer memory
622 treatment plan
624 magnetic resonance data
626 magnetic resonance image
628 registered location of target zone
630 radiotherapy control signals
632 positioning control signals
634 channel calibration
636 therapeutic control system module
638 image reconstruction module
640 image registration module
642 planning module
644 pre-calibration module

The invention claimed is:

1. A therapeutic apparatus comprising:
a radiotherapy apparatus for treating a target zone of a subject, wherein the radiotherapy apparatus comprises a radiotherapy source for directing a radiation beam into the target zone;
a magnetic resonance imaging system for acquiring magnetic resonance imaging data from an imaging zone, a subject support configured to support the subject with the target zone within the imaging zone, the subject support configured to move in three spatial directions and to rotate about an axis for each of those directions, allowing for free placement of a subject;
the magnetic resonance imaging system including a magnet for generating a magnetic field within the imaging zone defined in an inner bore of the magnet, wherein the radiotherapy apparatus is configured to rotate the radiotherapy source peripherally around the magnet and the subject supported in the target zone,
wherein the magnetic resonance imaging system does not comprise a radio frequency volume body coil mounted in the inner bore around the imaging zone, wherein the inner bore is at least 80 cm in diameter;
the magnetic resonance imaging system including
a split gradient coil disposed in the inner bore with a gap through which a path of the radiation beam passes as the radiotherapy source rotates peripherally around the subject, and at least two local radio-frequency transmit and receive channels positioned avoiding the path of the radiation beam generated by the radiotherapy source as the radiotherapy source rotates peripherally around the subject, the at least two local radio frequency transmit and receive channels being supported by at least one of the subject and the support, and configured to independently exclusively transmit radio frequency fields into the imaging zone for exciting and manipulating an orientation of magnetic spins in the imaging zone and to acquire the magnetic resonance data from the imaging zone, wherein the two local radio frequency transmit-and-receive channels are positioned to maintain a peripheral gap therebetween such that the channels avoid the path of the radiation beam as the radiation source rotates peripherally around the subject.

2. The therapeutic apparatus of claim 1, wherein the radiotherapy source rotates about an axis of rotation, wherein the subject support is configured to position the target zone in the imaging zone on the axis of rotation.

3. The therapeutic apparatus of claim 1, wherein the at least two local transmit-and-receive channels comprise flexible coil elements.

4. The therapeutic apparatus of claim 1, wherein the radiotherapy apparatus comprises a light source configured to illuminate a portion of the subject that is descriptive of the path of the radiation beam generated by the radiotherapy source.

5. The therapeutic apparatus of claim 1, wherein the at least two local radiofrequency transmit-and-receive channels include a first local transmit-and-receive channel and a second local transmit-and-receive channel and further including:
- a first transceiver connected with the first local transmit-and-receive channel; and
- a second transceiver, different from the first transceiver, connected with the second local transmit-and-receive channel;
- the first and second transceivers being connected with a processor to independently convey instructions to transmit the radio frequency excitation fields to the first and second local transmit-and-receive channels and to convey the magnetic resonance data to the processors.

6. The therapeutic apparatus of claim 1, wherein the at least two local transmit-and-receive channels include a first flexible local coil and a second flexible local coil, the first and second flexible local coils configured to be positioned around torso portions of a patient separated by the peripheral gap through which the radiation beam passes.

7. The therapeutic apparatus of claim 1, further comprising:
- a processor configured to control the therapeutic apparatus and the magnetic resonance imaging apparatus;
- a memory containing machine executable instructions for execution by the processor, wherein execution of the instructions causes the processor to:
  - perform a pre-scan calibration using the at least two local transmit-and-receive channels of the magnetic imaging system;
  - acquire the magnetic resonance data in accordance with the pre-scan calibration using the at least two transmit-and-receive channels;
  - reconstruct a magnetic resonance image from the magnetic resonance data;
  - register a location of the target zone in the magnetic resonance image;
  - generate radiotherapy control signals in accordance with the location of the target zone, wherein the radiotherapy control signals cause the radiotherapy source to irradiate the target zone with the radiation beam; and
  - send the radiotherapy control signals to the radiotherapy system.

8. The therapeutic apparatus of claim 7, wherein each of the local transmit-and-receive channels has multiple coil elements, wherein execution of the instructions further causes the processor to calibrate transmit amplitudes and phases and receive amplitudes and phases for the multiple coil elements during the pre-scan calibration.

9. The therapeutic apparatus of claim 7, wherein execution of the instructions further causes the processor to:
- repeatedly acquire the magnetic resonance data during the irradiation of the target zone, reconstruct the magnetic resonance image, and register the location of the target zone during irradiation of the target zone; and
- repeatedly generate and send updated radiotherapy control signals, wherein the updated radiotherapy control signals compensate for motion of the subject between subsequent acquisitions of the magnetic resonance data, wherein the updated radiotherapy control signals are sent to the radiotherapy source during irradiation of the target zone.

10. The therapeutic apparatus of claim 9, wherein the radiotherapy source comprises an adjustable beam collimator, wherein the updated radiotherapy control signals comprises commands for controlling the beam collimator.

11. The therapeutic apparatus of claim 9, wherein the magnet is a cylindrical super conducting magnet, wherein the magnet has a recess in an outer wall, wherein the radiotherapy apparatus is adapted for rotating the radiotherapy source around the recess, and wherein at least a portion of the radiotherapy source is within the recess.

12. A non-transitory, computer program product comprising machine executable instructions for execution by a processor of a therapeutic apparatus; wherein the therapeutic apparatus comprises a radiotherapy apparatus for treating a target zone of a subject;
wherein the radiotherapy apparatus comprises a radiotherapy source for directing a radiation beam into the target zone and a magnetic resonance imaging system for acquiring magnetic resonance imaging data from an imaging zone;
a subject support configured to support the subject with the target zone within the imaging zone, the subject support configured to move in three spatial directions and to rotate about an axis for each of the three spatial directions, allowing for free placement of a subject, the magnetic resonance imaging system including a cylindrical magnet for generating a magnetic field within the imaging zone defined in an inner bore of the magnet, wherein the radiotherapy apparatus is adapted for rotating the radiotherapy source around the magnet, the magnetic resonance imaging system including at least two local radio-frequency transmit and receive channels positioned avoiding a path of the radiation beam generated by the radiotherapy source, the at least two local radio frequency transmit and receive channels including first and second flexible local radio frequency transmit and receive coils disposed around a torso portion of the subject with a gap therebetween, the first and second flexible local radio frequency transmit and receive coils being supported by the subject and being adapted for independently transmitting radio frequency fields into the imaging zone for exciting and manipulating an orientation of magnetic spins in the imaging zone and for acquiring the magnetic resonance data from the imaging zone, wherein the at least two local radio frequency transmit-and-receive channels are positioned to maintain the gap therebetween, the radiation beam passing through the gap; and wherein execution of the instructions causes the processor to:

perform a pre-scan calibration using the at least two local transmit-and-receive channels of the magnetic resonance imaging system;

acquire the magnetic resonance data during irradiation of the target zone in accordance with the pre-scan calibration using the at least two local transmit-and-receive channels;

reconstruct magnetic resonance images from the magnetic resonance data which the radiation beam is directed into the target area;

register a location of the target zone in the magnetic resonance images;

generate radiotherapy control signals in accordance with the location of the target zone, wherein the radiotherapy control signals cause the radiotherapy source to irradiate the target zone; and send the radiotherapy control signals to the radiotherapy system.

13. A method of controlling a therapeutic apparatus, wherein the therapeutic apparatus comprises a radiotherapy apparatus for treating a target zone of a subject including a radiotherapy source for directing electromagnetic radiation into the target zone; wherein the therapeutic apparatus further comprises a magnetic resonance imaging system for acquiring magnetic resonance imaging data from an imaging zone; a subject support configured to support the subject with the target zone within the imaging zone, the subject support configured to move in three spatial directions and also be able to rotate about an axis for each of those directions, allowing for free placement of a subject; the magnetic resonance imaging system including a magnet for generating a magnetic field within the imaging zone defined in an inner bore of the magnet, wherein the inner bore is greater than or equal to 80 cm in diameter, wherein the radiotherapy apparatus is adapted for rotating the radiotherapy source at least partially around an outer periphery of the magnet, wherein the magnetic resonance imaging system does not comprise a radio frequency volume body coil mounted in the inner bore around the imaging zone, the magnetic resonance imaging system including at least two separate local radio-frequency transmit and receive channels positioned avoiding a path of radiation generated by the radiotherapy source, the at least two local radio frequency transmit and receive channels being supported by at least one of the subject and the support, and adapted for independently transmitting radio frequency fields for exciting magnetic spins and manipulating an orientation of the magnetic spins in the imaging zone and for acquiring the magnetic resonance data from the imaging zone, wherein the two local radio frequency transmit-and-receive channels are positioned to maintain a gap configured to avoid at least the path of the radiation; and wherein the method comprises the steps of:

performing a pre-scan calibration using the at least two local transmit-and-receive channels of the magnetic resonance imaging system;

acquiring the magnetic resonance data in accordance with the pre-scan calibration using the at least two local transmit-and-receive channels;

reconstructing a magnetic resonance image from the magnetic resonance data;

registering a location of the target zone in the magnetic resonance image; and generating radiotherapy control signals in accordance with the location of the target zone, wherein the radiotherapy control signals cause the radiotherapy source to irradiate the target zone; and sending the radiotherapy control signals to the radiotherapy system.

14. The method according to claim 13, wherein the at least two transmit and receive channels include first and second flexible coils disposed around a portion of the subject with the gap therebetween, the first and second coils being disposed such that the radiation beam passes through the gap between the first and second local coils as the radiation therapy source rotates relative to the subject.

15. The method of claim 14, wherein the first and second flexible local coils are disposed around torso portions of the subject.

16. The method of claim 14, wherein the magnetic resonance data is acquired during irradiation of the target zone.

17. A therapeutic apparatus comprising:

a radiotherapy apparatus configured to treat a target zone of a subject disposed in an inner bore of a magnet, the radiotherapy apparatus including a radiotherapy source configured to direct a radiation beam into the target zone, the radiation therapy source being configured to rotate at least partially around an outside periphery of the magnet;

a magnetic resonance imaging system configured to acquire magnetic resonance imaging data from an imaging zone defined in the inner bore, wherein the target zone is disposed within the imaging zone, the magnetic resonance imaging system including:

the magnet, the magnet being configured to generate a main magnetic field within the imaging zone in the inner bore, wherein the inner bore is greater than or equal to 80 cm in diameter, a subject support configured to support the subject in the inner bore with the target zone in the imaging zone, the subject support configured to move in three spatial directions and also be able to rotate about an axis for each of those directions, allowing for free placement of a subject, a gradient magnetic field coil configured to generate gradient magnetic field gradients across the imaging zone, the gradient magnetic field coil being mounted within the inner bore of the magnet, wherein there is no volume body coil for transmitting radio frequency magnetic resonance excitation fields or for receiving magnetic resonance data mounted in the inner bore of the magnet, a first local transmit-and-receive channel including a plurality of first coil elements configured to be supported by at least one of the support and the subject in the imaging volume adjacent the target zone and positioned to avoid a path of the radiation beam travelling from the radiotherapy source to the target zone, a second local transmit-and-receive channel including a plurality of second coil elements configured to be supported by at least one of the subject support and the subject in the imaging volume adjacent the target zone and positioned to avoid a path of the radiation beam travelling from the radiotherapy source to the target zone, a first transceiver connected with the first local transmit-and-receive channel,
a second transceiver connected with the second local transmit-and-receive channel,
wherein the first and second local transmit-and-receive channels are positioned to maintain a gap therebetween avoiding the path of the radiation beam,
wherein the first transceiver is configured to control the first local transmit-and-receive coil to generate a radiofrequency excitation field for exciting and manipulating the orientation of magnetic spins in the imaging zone,
wherein the second transceiver is configured to control the second local transmit-and-receive coil to generate radiofrequency excitation fields for exciting and manipulating the orientation of magnetic spins in the imaging zone,
wherein the first transceiver is configured to receive magnetic resonance data from the first local transmit-and-receive channel, and
wherein the second transceiver is configured to receive magnetic resonance data from the second local transmit-and-receive channel; and
a computer system including:
a hardware interface connected with the radiotherapy system, the gradient magnetic field coil, the first transceiver, and the second transceiver,
a memory containing machine-readable instructions executable by a computer processor, execution of the instructions by the computer processor causing the hardware interface to:
send instructions to at least the first and second transceivers to perform a pre-scan calibration of at least the first and second local transmit-and-receive channels,
receive the magnetic resonance data from the first and second transceivers,
receive the magnetic resonance data from the first and second transceivers and reconstruct the received magnetic resonance data into a magnetic resonance image,
register a location of the target zone in the magnetic resonance image, and
control the hardware interface to send radiotherapy control signals in accordance with the location of the target zone to control the radiotherapy source to irradiate the target zone.

18. The therapeutic apparatus of claim 17, wherein the first and second transceivers are configured to independently convey instructions to transmit the radio frequency excitation fields to the first and second local transmit-and-receive channels and to convey the magnetic resonance data to the computer system.

19. The therapeutic apparatus of claim 17, wherein the magnet is a cylindrical super conducting magnet, wherein the magnet has a recess in an outside peripheral wall, wherein the radiotherapy apparatus is configured to rotate the radiotherapy source around the magnet with at least a portion of the radiotherapy source disposed within the recess in the outside peripheral wall.

20. The method according to claim 17, wherein the first and second local transmit-and-receive channels include first and second flexible coils disposed around a portion of the subject with the gap therebetween, the first and second flexible coils being disposed such that the radiation beam passes through the gap between the first and second local coils as the radiation therapy source rotates relative to the subject, wherein the first and second flexible local coils are disposed around torso portions of the subject, wherein the magnetic resonance data is acquired during irradiation of the target zone, wherein the control signals are generated and updated to compensate for subject motion.

* * * * *